United States Patent [19]
Stevenson et al.

[11] Patent Number: 5,476,937
[45] Date of Patent: Dec. 19, 1995

[54] S-TRIAZINE UV ABSORBERS SUBSTITUTED BY A SULFUR-CONTAINING MOIETY

[75] Inventors: Tyler A. Stevenson, Teaneck, N.J.; Mark S. Holt, West Nyack; Ramanathan Ravichandran, Nanuet, both of N.Y.

[73] Assignee: Ciba-Geigy Corporation, Tarrytown, N.Y.

[21] Appl. No.: 268,093

[22] Filed: Jun. 28, 1994

Related U.S. Application Data

[60] Division of Ser. No. 189,627, Feb. 1, 1994, Pat. No. 5,354,794, which is a continuation-in-part of Ser. No. 12,699, Feb. 3, 1993, abandoned.

[51] Int. Cl.$^6$ .................................................. C07D 251/12
[52] U.S. Cl. ......................................................... 544/216
[58] Field of Search ............................................... 544/216

[56] References Cited

U.S. PATENT DOCUMENTS

| | | | |
|---|---|---|---|
| 3,118,887 | 1/1964 | Hardy et al. | 544/216 |
| 3,242,175 | 3/1966 | Duennenberger et al. | 544/216 |
| 3,244,708 | 4/1966 | Duennenberger et al. | 544/216 |
| 3,268,474 | 8/1966 | Hardy et al. | 264/252 |
| 4,355,071 | 10/1982 | Chang | 428/334 |
| 4,619,956 | 10/1986 | Susi | 524/87 |
| 4,740,542 | 4/1988 | Susi | 524/87 |
| 4,826,978 | 5/1989 | Migdal et al. | 544/216 |
| 4,962,142 | 10/1990 | Migdal et al. | 524/100 |
| 5,298,067 | 3/1994 | Valet et al. | 524/100 |
| 5,322,868 | 6/1994 | Valet et al. | 524/89 |

FOREIGN PATENT DOCUMENTS

| | | |
|---|---|---|
| 0442847 | 8/1991 | European Pat. Off. . |
| 444323 | 9/1991 | European Pat. Off. . |
| 483488 | 5/1992 | European Pat. Off. . |

*Primary Examiner*—Kriellion S. Morgan
*Attorney, Agent, or Firm*—Luther A. R. Hall

[57] ABSTRACT

Tris-aryl-s-triazine UV absorbers typified by those of formula B or C

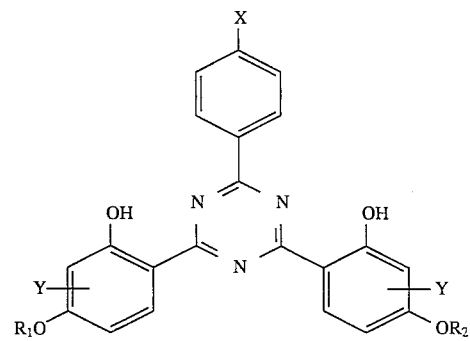

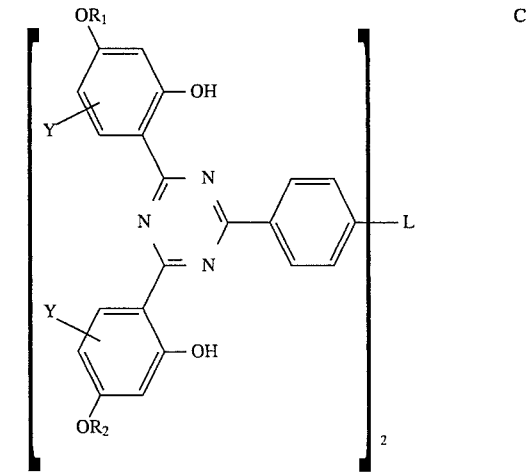

wherein X and L each possess a sulfur-containing moiety, provide excellent light stability protection to electro coat, base coat or clear coat finishes.

2 Claims, No Drawings

S-TRIAZINE UV ABSORBERS SUBSTITUTED BY A SULFUR-CONTAINING MOIETY

This is a divisional of application Ser. No. 08/189,627, filed Feb. 1, 1994, now U.S. Pat. No. 5,354,794, issued on Oct. 11, 1994, which is a continuation-in-part of application Ser. No. 08/012,699, filed on Feb. 3, 1993, now abandoned.

The instant invention pertains to polymer film coating compositions protected against catastrophic delamination by the presence of selected tris-aryl-s-triazines.

BACKGROUND OF THE INVENTION

Tris-aryl-s-triazines in which at least one of the aryl groups has an hydroxy group ortho to the point of attachment to the s-triazine ring are well-known UV absorber light stabilizers. Such tris-aryl-s-triazines protect organic polymers from the deleterious effects of actinic light.

U.S. Pat. Nos. 3,118,887 and 3,268,474 describe the stabilization of plastic and resinous compositions from UV light by the incorporation of one or more compounds of the class of tris-aryl-s-triazines. The preferred UV absorbers of these inventions are symmetrical tris-(o-hydroxyphenyl)-s-triazines further substituted in the aryl moieties at the 4-position by either an hydroxy or alkoxy moiety. These patents point out that these UV absorbers may be used in coatings based on oil-modified alkyd resins. It is also pointed out that an effective UV absorber should not absorb at all in the visible range so that it exhibits no yellow color visually.

U.S. Pat. Nos. 3,242,175 and 3,244,708 disclose 2,4,6-tris-(2,4-dihydroxyphenyl)-s-triazine and 2,4-bis-(2,4-dihydroxyphenyl)-6-phenyl-s-triazine. The phenyl group of the bis-dihydroxyphenyl compounds may be substituted by halogen, lower alkyl, lower alkoxy or phenyl, preferably in the para position relative to the point of attachment to the s-triazine ring. One or more of the hydroxy groups, preferably those in the para position, of the dihydroxyphenyl rings may be derivatized with alkyl, alkenyl, hydroxyalkyl, hydroxyalkoxyalkyl, halogenoalkyl, cyanoalkyl, carboxyalkyl, carbalkoxyalkyl, phenylalkyl or halogenophenylalkyl groups. These patents also disclose lacquers and films of diverse composition and natural or synthetic resins among other organic materials which may be stabilized from the harmful effects of heat, oxygen and especially actinic light. These patents also disclose that the UV absorbers may be employed in a "filter layer" which would protect the substrate directly beneath said layer or at some distance from it.

U.S. Pat. Nos. 4,619,956 and 4,740,542 disclose the use of synergistic amounts of tris-aryl-s-triazines and hindered amine light stabilizers in polymer film coatings or molded articles against the action of light, moisture and oxygen. Preferably these coatings are acid catalyzed thermoset acrylic or alkyd coatings and most preferably high solids thermoset acrylic coatings. The tris-aryl-s-triazines referred to in these patents are those described in U.S. Pat. Nos. 3,118,887 and 3,268,474. The preferred s-triazine is 4,6-bis-(2,4-dimethylphenyl)-2-(2,4-dihydroxyphenyl)-s-triazine or 4,6-bis-(2,4-dimethylphenyl)-2-(2-hydroxy-4 -octyloxy-phenyl)-s-triazine.

U.S. Pat. Nos. 4,826,978 and 4,962,142 disclose a class of tris-aryl-s-triazines useful as ultraviolet screens for polymers, including films and coatings. This subgenus of tris-aryl-s-triazines is substituted at the 2 and 4 positions of the s-triazine ring by a 2,4-dihydroxyphenyl group. The para hydroxy moiety is derivatized with an hydroxyalkyl or an alkylcarboxylate group, specifically either a 2-hydroxyethyl or 2-acetoxyethyl moiety. These specific functional groups allow the LrV absorber to become chemically bonded to the polymer being stabilized and therefore are non-extractable. These triazines are further substituted in the 6-position of the s-triazine ring by a phenyl group which is substituted by an electron withdrawing group, preferably halogen, cyano, trifluoromethyl, nitro or acetoxy. These s-triazines are touted as non-yellowing presumedly due to the electron withdrawing substituent on the 6-phenyl moiety.

U.S. Pat. No. 4,355,071 describes stabilized clear coat/color coat systems for automobiles and trucks and teaches that 1–20% by weight of an ultraviolet stabilizer should be incorporated into the color coat. The UV stabilizer will migrate to the upper clear coat and will continue to do so as it is lost from the clear coat due to weathering. Because of this mechanism of action, there will presumedly always be an adequate concentration of UV stabilizer in the clear coat to protect the entire coating system from deterioration. UV stabilizers mentioned in this context include benzophenones, triazoles, triazines, benzoates, etc.

European published application No. 444,323 describes the stabilization of high solids coatings with selected s-triazine UV absorbers, typified by 2,4-di(2,4-dimethylphenyl)-6-[2-hydroxy-4-O(mixed alkyl)phenyl]-s-triazine.

European published application No. 483,488 describes the synergistic combination of a hindered amine and a selected s-triazine UV absorber for the stabilization of polymers including thermoset acrylic coatings. The s-triazine UV absorbers are typified by 2,4-di(2,4-dimethylphenyl)-6-[2-hydroxy-4-(3-ethylhexyl-2-hydroxy-1-propoxy] phenyl-s-triazine. These compounds and compositions are related to the compounds and compositions of copending application Ser. No. 08/143,525.

U.S. Pat. No. 5,300,414 describes compounds which are useful in photographic applications and which are similar to the instant compounds of formula A.

A coating system commonly used for automobile and truck finishes consists of an electro coat primer, a pigmented base or color coat and a top clear coat. A particular problem occurring with this system is delamination, i.e. a peeling away of the coating from the substrate. It has been found that the cause of delamination is deterioration of the electro coat due to the effects of ultraviolet light that passes through both the base coat and the clear coat. It has now been found that a subgenus of tris-aryl-s-triazines, those based on 2,4,6-tris-(2,4-dihydroxyphenyl)-s-triazine and 2,4-bis-(2,4-dihydroxyphenyl)-s-triazine, is particularly effective in protecting the electro coat of this system when incorporated into either the base coat or the clear coat or both. This significantly inhibits the undesired delamination. Although the prior art points out that a wide variety of tris-aryl-s-triazines are generally useful as ultraviolet screening agents for coatings, the particular utility of this selected subgenus of compounds for the purpose of preventing such catastrophic delamination events is neither disclosed nor suggested.

The instant subgenus of tris-aryl-s-triazines have significant absorbance in the range of 360–400 nm, and in some cases beyond 400 nm. Because these compounds absorb towards the visible spectrum, they are yellow in color. It is believed that the increased absorbance in this region as compared to tris-aryl-s-triazines in general is responsible for the excellent delamination protection afforded by the instant compounds in these coating systems.

Additionally, the instant invention does not require the presence of a hindered amine light stabilizer, but does require that: s-triazine derivative of component (d) contain at least two groups on the triazinyl moiety be derived from resorcinol. This distinguishes the instant invention from the closest prior art where only one group on the triazinyl moiety derived from resorcinol is uniformly present in the closest prior art compounds and compositions.

The majority of the compounds disclosed are functionalized with alkyl groups containing at least two oxygen atoms and are more soluble in common coatings solvents than tris-aryl-s-triazines that are functionalized with simple alkyl groups. Common coatings solvents include xylene, methyl amyl ketone, butyl cellosolve, butyl carbitol and methyl isobutyl ketone. This functionality in combination with the high molecular weight of the compounds provides the instant compounds with a low migratory propensity when incorporated into the base coat of a clear coat/base coat system. Because the instant compounds are inherently yellow, minimum migration of the instant compounds into the clear coat is desirable.

OBJECTS OF THE INVENTION

The object of this invention is to provide a method for protecting an electro coat/base coat/clear coat coating system against delamination from a substrate by incorporating therein a selected type of tris-aryl-s-triazine.

Another object of this invention is to provide some novel tris-aryl-s-triazines of value for carrying out the instant method.

DETAILED DISCLOSURE

The instant invention pertains to a polymer film composition which comprises (a) an electro coat primer in adhesion to a metal substrate; (b) a base or color coat that is in adhesion to the electrocoat and which comprises a film-forming binder and an organic pigment or an inorganic pigment or mixture thereof; (c) a clear coat that is in adhesion to the base coat and which comprises a film-forming binder, and (d) an effective stabilizing mount, between 1 and 20% by weight of the film-forming binder, of at least one tris-aryl-s-triazine UV absorber contained in either the base coat or the clear coat or in both base coat and clear coat, preferably in the base coat.

More particularly, the instant tris-aryl-s-triazines have formula A, B or C

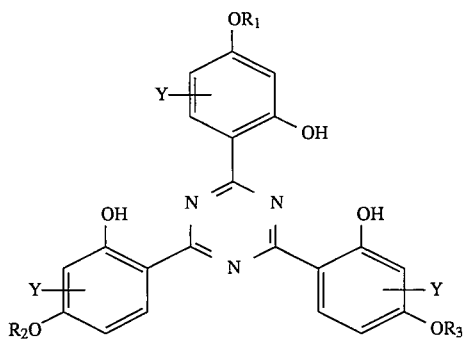

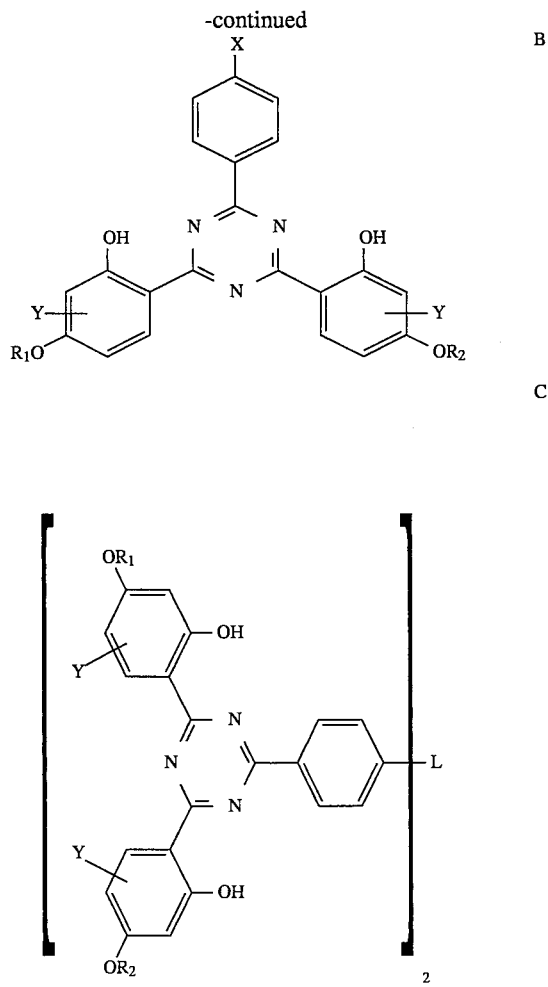

wherein
$R_1$, $R_2$, and $R_3$ are the same or different and are hydrogen or straight or branched chain alkyl of 1 to 24 carbon atoms; or said alkyl substituted by one to eight halogen, —$R_4$, —$OR_5$, —$N(R_5)_2$, —$CON(R_5)_2$, —$COOR_5$, or —$OCOR_5$ groups or combinations thereof; or said alkyl interrupted by one to eight —O—, —$NR_5$—, —$CONR_5$—, —COO—, —OCO—, or —CO— groups or combinations thereof; or said alkyl both substituted and interrupted by combinations of the groups mentioned above;

$R_4$ is cycloalkyl of 5 to 12 carbon atoms, straight or branched chain alkenyl of 2 to 18 carbon atoms, phenyl, naphthyl, biphenyl, or said phenyl, said naphthyl or said biphenyl substituted by one to three halogen, alkyl of 1 to 8 carbon atoms, alkoxy of 1 to 8 carbon atoms or combinations thereof; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof;

$R_5$ is defined as is $R_4$, or $R_5$ is also hydrogen or straight or branched chain alkyl of 1 to 24 carbon atoms, Y is hydrogen or straight or branched chain alkyl of 1 to 6 carbon atoms;

X is hydrogen, straight or branched chain alkyl of 1 to 4 carbon atoms, phenyl, halogen, —$SR_6$, —$SOR_6$ or —$SO_2R_6$, where $R_6$ is alkyl of 1 to 20 atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms; and L is —S—, —SO—, —SO$_2$—, —S—S—, —S—E—S—, —SO—E—SO— or —SO$_2$—E—SO$_2$—, where E is alkylene of 2 to 12 carbon atoms, cycloalkylene of 5 to 12 carbon atoms or alkylene interrupted by or terminated by cyclohexylene; and with the proviso that when X is halogen, R$_1$ and R$_2$ together are not —CH$_2$CH(R$_7$)OR$_8$ where R$_7$ is hydrogen or methyl, and R$_8$ is hydrogen or —COR$_9$ where R$_9$ is alkyl of 1 to 6 carbon atoms.

Preferably, the instant invention pertains to compounds of formula I or II

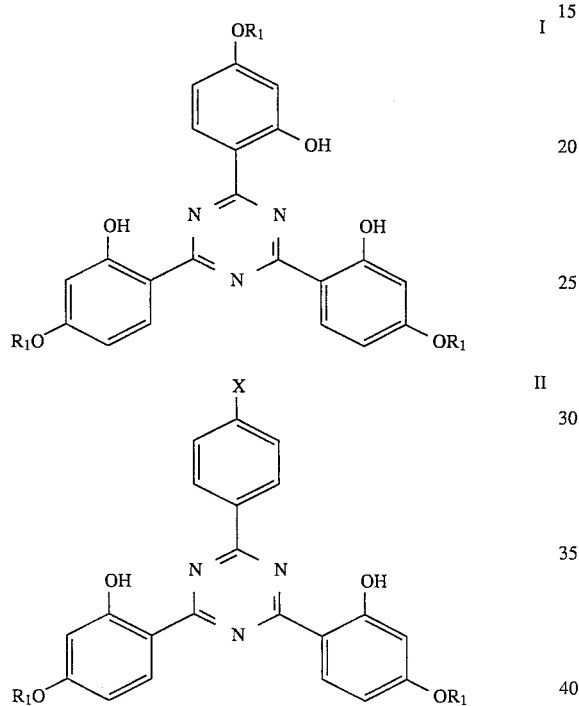

where

R$_1$ is straight or branched chain alkyl of 2 to 24 carbon atoms, or said alkyl substituted by one or two —OR$_5$, where R$_5$ is hydrogen, straight or branched chain alkyl of 1 to 24 carbon atoms, phenyl or said phenyl substituted by one to three halogen, alkyl of 1 to 8 carbon atoms or alkoxy of 1 to 8 carbon atoms;

X is hydrogen, straight or branched chain alkyl of 1 to 4 carbon atoms, phenyl, halogen, —SR$_6$, —SOR$_6$ or —SO$_2$R$_6$, where R$_6$ is alkyl of 1 to 20 carbon atoms or aryl of 6 to 10 carbon atoms; and with the proviso that when X is halogen, R$_1$ is not —CH$_2$CH(R$_7$)OH where R$_7$ is hydrogen or methyl.

Most preferably, R1 is straight or branched chain alkyl of 2 to 6 carbon atoms or said alkyl substituted by one or two —OR$_5$, where R$_5$ is hydrogen, straight or branched chain alkyl of 1 to 24 carbon atoms or phenyl; X is hydrogen, straight or branched chain alkyl of 1 to 4 carbon atoms, chloro, —SR$_6$, —SOR$_6$ or —SO$_2$R$_6$, where R$_6$ is phenyl; and with the proviso that when X is chloro, R$_1$ is not —CH$_2$CH(R$_7$)OH where R$_7$ is hydrogen or methyl.

Examples of R$_1$, R$_2$ and R$_3$ are —CH$_2$CH(OH)CH$_2$OC$_8$H$_{17}$, —CH$_2$CH(OH)CH$_2$OC$_{10}$H$_{21}$, —CH$_2$CH(OH)CH$_2$OC$_{12}$H$_{25}$, —CH$_2$CH(OH)CH$_2$OCH(CH$_3$)$_2$, —CH$_2$CH(OH)CH$_2$OC$_6$H$_5$,

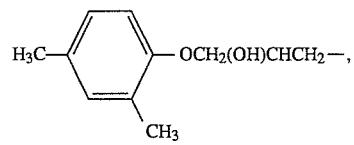

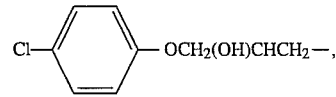

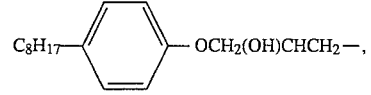

—CH$_2$COOH, and —CH$_2$COOOC$_8$H$_{17}$. The instant invention also pertains to novel tris-aryl-s-triazine UV absorbers of formula B or C

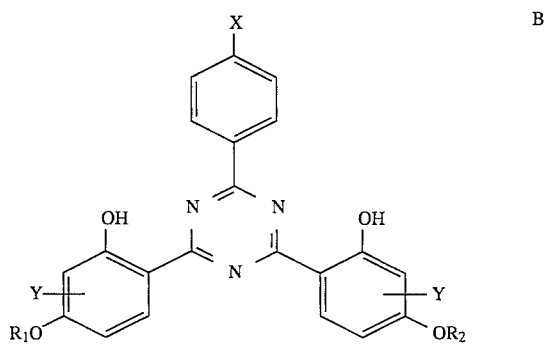

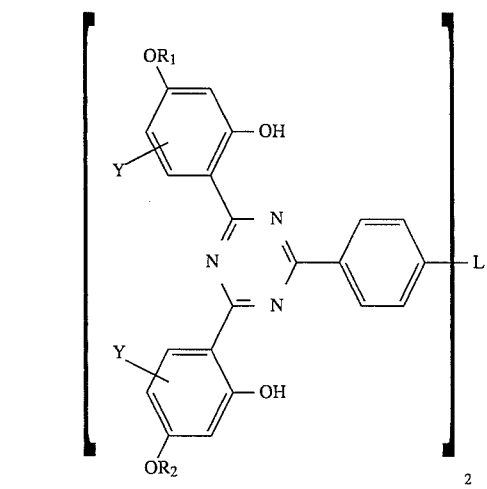

wherein

R$_1$ and R$_2$ are the same and are —CH$_2$CH(OH)CH$_2$OR$_5$,

R$_5$ is straight or branched chain alkyl of 1 to 24 carbon atoms, phenyl or said phenyl substituted by one to three halogen, alkyl of 1 to 8 carbon atoms, alkoxy of 1 to 8 carbon atoms or combinations thereof; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof;

Y is hydrogen or straight or branched chain alkyl of 1 to 6 carbon atoms;

X is hydrogen, straight or branched chain alkyl of 1 to 4 carbon atoms, phenyl, phenyl substituted by alkyl of 1 to 4 carbon atoms, —$SR_6$, —$SOR_6$ or —$SO_2R_6$, where $R_6$ is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms;

L is —S—, —SO—, —$SO_2$—, —S—S—, —S—E—S—, —SO—E—SO— or —$SO_2$—E—$SO_2$—, where E is alkylene of 2 to 12 carbon atoms, cycloalkylene of 5 to 12 carbon atoms or alkylene interrupted by or terminated by cyclohexylene; and with the proviso that, when X is —$SR_6$, —$SOR_6$ or —$SO_2R_6$, $R_1$ and $R_2$ can also be the same or different and are hydrogen or straight or branched chain alkyl of 1 to 24 carbon atoms; or said alkyl substituted by one to eight halogen, —$R_4$, —$OR_5$, —$N(R_5)_2$, —$CON(R_5)_2$, —$COOR_5$, or —$OCOR_5$ groups or combinations thereof; or said alkyl interrupted by one to eight —O—, —$NR_5$—, —$CONR_5$—, —COO—, —OCO—, or —CO—groups or combinations thereof; or said alkyl both substituted and interrupted by combinations of the groups mentioned above;

$R_4$ is cycloalkyl of 5 to 12 carbon atoms, straight or branched chain alkenyl of 2 to 18 carbon atoms, phenyl, naphthyl, biphenyl, or said phenyl, said naphthyl or said biphenyl substituted by one to three halogen, alkyl of 1 to 8 carbon atoms, alkoxy of 1 to 8 carbon atoms or combinations thereof; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof; and $R_5$ is defined as is $R_4$, or $R_5$ is also hydrogen or straight or branched chain alkyl of 1 to 24 carbon atoms.

The alkyd resin lacquers which can be stabilized against the action of light and moisture in accordance with the instant invention are the conventional storing lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycoufil resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

To attain maximum light stabilization, the concurrent use of other conventional light stabilizers can be advantageous. Examples of such stabilizers are UV absorbers of the benzophenone, benzotriazole, cyanoacrylate or oxanilide type, or metal-containing light stabilizers, for example, organic nickel compounds, or hindered amine light stabilizers. In two-coat systems, these additional light stabilizers can be added to the dear coat or both in the clear coat and in the pigments base coat.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutactiene, as well as polymers of cycloolefins, for instance of cyclopentene or norbornene.

2. Mixtures of the polymers mentioned under 1 ), for example mixtures of polypropylene with polyisobutylene.

3. Copolymers of monoolefins and diolefins with each other or with other vinyl monomers, such as, for example, ethylene/propylene. propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(α-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graff copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetates thereof, such as polyvinyl alcohol, polyvinyl acetate, polyvinyl stearate, polyvinyl benzoate, polyvinyl maleate, polyvinylbutyral, polyallyl phthalate or polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthaiamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyetheresters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC, rMBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed from about 1 to about 20% by weight of the stabilized composition, although this will vary with the particular substrate and application. An advantageous range is from 1 to 5%; preferably 1.5 to 2.5%.

The resulting stabilized compositions of the instant invention may optionally also contain from about 0.01 to about 5%, preferably from about 0.025 to about 2%, and especially from about 0.1 to about 1% by weight of various conventional additives, such as the materials listed below, or mixtures thereof.

Other compositions of special interest include those which additionally contain a UV absorber selected from the group consisting of the benzophenones, benzotriazoles, cyanoacrylic acid derivatives, hydroxyaryl-s-triazines, organic nickel compounds and oxanilides.

Preferred UV absorbers are selected from the group consisting of 2-[2-hydroxy-3,5-di-(α,α-dimethylbenzyl)phenyl]-2H-benzotriazole, 2-(2-hydroxy-3,5-di-tert-amylphenyl)-2H-benzotriazole, 2-[2-hydroxy-3-tert-butyl-5-(ω-hydroxy-octa(ethyleneoxy)carbonyl)ethylphenyl]-2H-benzotriazole, 2-[2-hydroxy-3-tert-butyl-5-(2-octyloxycarbonylethyl)phenyl]-2H-benzotriazole, 4,4'-dioctyloxyoxanilide, 2,2'-dioctyloxy-5,5'-di-tert-butyloxanilide, 2,2'-didodecyloxy-5,5'-di-tertbutyloxanilide, 2-ethoxy-2'ethyloxanilide, 2,6-bis(2,4-dimethylphenyl)-4-(2-hydroxy-4-octyloxyphenyl-s-triazine, 2,6-bis(2,4-dimethylphenyl)-4 -(2,4-dihydroxyphenyl)-s-triazine, 2,4-bis(2,4-dihydroxyphenyl)-6-(4-chlorophenyl)-s-triazine, 2,6-bis(2,4-dimethylphenyl)-4-[2-hydroxy-4-(2-hydroxy-3-dodecyloxypropanoxy)-phenyl]-s-triazine and 2,2'-dihydroxy-4,4'-dimethoxybenzophenone.

Additional compositions of interest include those which additionally contain an effective stabilizing amount of a phenolic antioxidant; those which additionally contain a hindered amine derivative; or which additionally contain a phosphite or phosphonite stabilizer.

Compositions of special interest also include those wherein the organic material is an enamel of high solids content used for an industrial finish; is used as a coil coating; is used as a penetrating wood finish or is used as a film-forming wood finish.

When the instant compounds also contain a reactive functional group, said compounds can be chemically bonded by either condensation or free radical addition reaction to the polymer substrate. This provides for a non-migrating, non-sublimable UV absorber stabilizer. Such reactive functional groups include hydroxy, amino, amido, carboxyl and ethylenically unsaturated moieties.

The various organic materials useful in the instant invention are described in detail later in this application as well as are the various coadditives whose concomitant use with the instant compounds is often found to be highly beneficial.

The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
  1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
  1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
  1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
  1.4. Alkylidene-bisphenols, for example
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.
  1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
  1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine  octyl-N-(3,5-di-tert-butyl-4-hydroxyphenyl)-carbamate
  1.7. Esters of β-(3,5-di-tert-butyl-4-hydroxyphenyl)-propionic acid with monohydric or polyhydric alcohols, for example, methanol diethylene glycol octadecanol triethylene glycol 1,6-hexanediol pentaerythritol diethylene glycol triethylene glycol pentaerythritol neopentyl glycol thiodiethylene glycol tris-hydroxyethyl isocyanurate di-hydroxyethyl oxalic acid diamide
  1.8. Esters of β-(5-tert-butyl-4-hydroxy-3-methylphenyl)-propionic acid with monohydric or polyhydric alcohols, for example, methanol octadecanol 1,6-hexanediol neopentyl glycol thiodiethylene glycol diethylene glycol triethylene glycol pentaerythritol tris-hydroxyethyl isocyanurate di-hydroxyethyl oxalic acid diamide
  1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers
  2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5' -di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert octyolamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone).

2.7. Oxalic acid diamides, for example, 4,4'-di-octyloxyoxanilide, 2,2'-di-octyloxy-5,5'-tert-butyl-oxanilide, 2,2'-didodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]- 6-(4-chlorophenyl)-s-triazine; 2,4-bis[2-hydroxy-4-(2-hydroxy-4-(2-hydroxyethoxy)phenyl] -6-(2,4-dimethylphenyl)-s-triazine; 2,4-bis[2-hydroxy-4-(2-hydroxyethoxy)phenyl- 6-(4-bromophenyl)-s-triazine; 2,4-bis[2-hydroxy-4-(2-acetoxyethoxy)phenyl]-6-(4 -chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloyl-hydrazine, N,N'-bissalicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyldithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmirate, antimony pyrocatecholate or zinc pyrocatecholate.

10. Nuclearing agents, for example, 4-tert-butyl-benzoic acid, adipic acid, diphenylacetic acid.

11. Fillers and reinforcing agents., for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)-benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl- 3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5 -di-tert-butyl-4-hydroxybenzyl)mesitol, hexmethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5 -di-tert-butyl- 4-hydroxyhydrocinnamate), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyloxy)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-ten-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4 -hydroxybenzyl)isocyanurate, 2,6-di-tert-butyl-p-cresol or 2,2'-ethylidenebis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl)nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis( 1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]undecane)diethyl] 1,2,3,4-butanetetracarboxylate, mixed [1,2,2,6,6-pentamethylpiperidin-4-yl/β,β,β',β'-tetramethyl-3,9 -(2,4,8,10-tetraoxaspiro[5.5]undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yl-n-dodecylsuccinimide, 1-acetyl13-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane. di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The following examples are presented for the purpose of illustration only and are not to be construed to limit the nature or scope of the instant invention in any manner whatsoever.

EXAMPLE 1

2,4,6-Tris-[2-hydroxy-4-(2-hydroxy-3-nonyloxypropoxy)phenyl]-s-triazine

To a 200 mL 3-necked, round bottomed flask equipped with a magnetic stirrer, condenser, thermometer and nitrogen atmosphere are charged 3.0 g (7.40 mmol) of 2,4,6-tris-(2,4-dihydroxyphenyl)-s-triazine, 22.5 g (0.11 mol) of glycidyl nonyl* ether, 220 mg of triphenylethylphosphonium iodide and 15 mL of mesitylene. The viscous suspension is heated to 175° C. with stirring. After about 20 minutes the mixture becomes homogeneous and the reaction is complete as monitored by thin layer chromatographic analysis. After hearing at 175° C. for a total of 30 minutes, the reaction mixture is allowed to cool to room temperature. The solution is then diluted with ethyl acetate, washed twice with water and once with brine and finally dried over anhydrous magnesium sulfate. The dried organic layer is then filtered and subjected to reduced pressure to remove the solvent and excess epoxide reactant and to afford an orange oil. This oil is purified with medium pressure chromatography with 1:1 heptane:ethyl acetate to afford 5.9 g (74%) yield of the title compound as an amber waxy solid.

*Nonyl is used in the context of this invention as a mixture of glycidyl octyl ether and glycidyl decyl ether and is derived from "Epoxide 7" which is a mixture of said glycidyl ethers available from CIBA-GEIGY Corporation. Wherever the term "nonyl" occurs in the working Examples it is meant to be a mixture of octyl and decyl averaging out as nonyl.

$^1$H nmr (CDC$_3$) and IR spectra are consistent with the desired compound; UV $\lambda_{max}$ (ethyl acetate) 305, 353 nm (ε30,200, 51,800).

EXAMPLE 2

6-(p-Chlorophenyl)-2,4-bis-[2-hydroxy-4(2-hydroxy-3-nonyloxypropoxy)phenyl]-s-triazine Following the general procedure of Example 1, 5.0 g (0.015 mol) of 6-(p-chlorophenyl)-2,4-bis-(2,4-dihydroxyphenyl)-s-triazine, 8.0 g (0.036 mol) of glycidyl nonyl ether, 300 mg of triphenylethylphosphonium iodide and 10 mL of mesitylene are reacted at 175° C. for 3.25 hours. The product is worked up by the procedure given in Example 1 to afford 5.6 g (51%) yield of the title compound as a yellow solid.

$^1$H nmr (CDCl$_3$) and mass spectra are consistent with the desired compound; UV $\lambda_{max}$ (ethyl acetate) 297, 354 nm (ε33,200, 34,500).

EXAMPLE 3

2,4-Bis-[2-hydroxy-4-(2-hydroxy-3-nonyloxypropoxy)-phenyl]-6-phenyl-s-triazine

Following the general procedure of Example 1, 9.46 g (0.025 mol) of 2,4-bis-(2,4-dihydroxyphenyl)-6-phenyl-s-triazine, 13.7 g (0.061 mol) of glycidyl nonyl ether, 450 mg of triphenylethylphosphonium iodide and 17 mL of mesitylene are reacted at 175° C. for two hours. The resultant brown solution is worked up by the procedure of Example 1 to afford 15.7 g (81%) yield of the title compound as a yellow solid.

$^1$H nmr (CDCl$_3$) and mass spectra are consistent with the desired compound; UV $\lambda_{max}$ (ethyl acetate) 296, 354 nm ($\epsilon$34,100, 41,100).

EXAMPLE 4

2,4-Bis-(2,4-dihydroxyphenyl)-6-[4-(phenylthio)-phenyl]-s-triazine

To a 500 mL round bottomed flask equipped with a magnetic stirrer, condenser, Dean-Stark trap and nitrogen atmosphere are charged 16.1 g (0.0394 mol) of 6-(p-chlorophenyl)-2,4-bis-(2,4-dihydroxyphenyl)-s-triazine, 2.72 g (0.0197 mol) of potassium carbonate, 600 mg of potassium iodide and 150 mL of N,N-dimethylformamide. A preheated oil bath (150° C.) is then applied to the stirred brown solution. Thiophenol (4.04 mL, 0.00394 mol) is added all at once through a syringe. The mixture is stirred at 150° C. for 4.5 hours and then allowed to cool to room temperature. The solution is diluted with water and extracted thrice with ethyl acetate. The combined organic layers are washed twice with 0.1N hydrochloric acid and then dried over anhydrous magnesium sulfate. The solvent is then removed under reduced pressure to give a yellow product. There is some unsolubilized material found at the interface in the ethyl acetate extractions of the reaction mixture which is washed with water and triturated with heptane. Both crops of yellow solid are the title compound and are combined to afford the title compound in a yield of 17.5 g (92%); mp>250°.

$^1$H nmr (methyl sulfoxide-d$_6$) is consistent with the desired product.

EXAMPLE 5

2,4-Bis-(4-butoxy-2-hydroxyphenyl)-6-[4-(phenylthio)-phenyl]-s-triazine

To a 500 mL round bottomed flask equipped with a magnetic stirrer, condenser and nitrogen atmosphere are charged 2.0 g (4.2 mmol) of 2,4-bis-(2,4-dihydroxyphenyl)-6-[4-(phenylthio)phenyl]-s-triazine, 0.58 g (4.2 mmol) of potassium carbonate and 30 mL of N,N-dimethylformamide. The mixture is heated to 90° C., and the s-triazine compound dissolves readily. Bromobutane (4.5 mL, 42.0 mmol) is added all at once. The reaction mixture is heated at 90° C. for 2.5 hours and then stirred at room temperature overnight yielding a yellow precipitate. Chilled water is added and the yellow precipitate is isolated by vacuum filtration to give 2.74 g of crude product. The crude product is purified by flash chromatography with 1:1 heptane:ethyl acetate to afford 0.26 g (10%) yield of the title compound as a yellow solid; mp>250°.

Analysis: Calcd for C$_{35}$H$_{35}$N$_3$O$_4$S: C, 70.8; H, 5.9; N, 7.1. Found: C, 70.4; H, 5.9; N, 7.1.

EXAMPLE 6

2,4-Bis-[2-hydroxy-4-(2-hydroxy-3-nonyloxypropoxy)-phenyl]-6-[4-(phenylthio)phenyl]-s-triazine Following the general procedure of Example 1, 17.5 g (0.0364 mol) of 2,4-bis-(2,4-dihydroxyphenyl)-6-[4-(phenylthio)phenyl]-s-triazine, 20.0 g (0.0890 mol) of glycidyl nonyl ether, 0.65 g of triphenylethylphosphonium iodide and 37 mL of mesitylene are heated at 185° C. for two hours. The product is worked up by the procedure of Example 1 to yield about 40 g of a brown oil. The oil is purified by medium pressure chromatography with 2:1 heptane:ethyl acetate to afford 24.6 g (80%) yield of the title compound as an orange waxy solid.

$^1$H nmr (CDCl$_3$) and mass spectra are consistent with the desired compound; UV $\lambda_{max}$ (CHCl$_3$) 304, 354 nm ($\epsilon$28,300, 64,300).

EXAMPLE 7

6-[4-(Benzenesulfonyl)phenyl]-2,4-bis-[2-hydroxy-4-(2-hydroxy-3-nonyloxypropoxy)-phenyl]-s-triazine To a 500 mL round bottomed flask equipped with a magnetic stirrer are charged 11.7 g (0.0138 mol) of 2,4-bis-[2-hydroxy-4-(2-hydroxy-3-nonyloxypropoxy)phenyl]-6-[4-(phenylthio)phenyl]-s-triazine and 150 mL of chloroform. The stirred solution is cooled in an ice bath and 9.5 g (0.0276 mol) of m-chloroperoxybenzoic acid (50–60%) are added quickly in small portions. The mixture is stirred for two hours at 5° C. followed by another two hours at room temperature. The solvent is then removed under reduced pressure and the residue taken up in ethyl acetate. The resulting solution is washed once with 10% sodium sulfite solution, then five times with saturated sodium bicarbonate solution and once with brine. After drying the organic layer over anhydrous magnesium sulfate, the solvent is removed and the residue is purified by medium pressure liquid chromatography with 1:1 heptane:ethyl acetate which is graded to 1:3 heptane:ethyl acetate to afford 11.3 g (93%) yield of the title compound as a yellow glass.

$^1$H nmr (CDCl$_3$) and mass spectra are consistent with the desired compound; UV $\lambda_{max}$ (CHCl$_3$) 300, 360 nm ($\epsilon$33,700, 35,000).

EXAMPLE 8

6-[4-(Benzenesulfinyl)phenyl]-2,4-bis-[2-hydroxy-4-(2-hydroxy-3-nonyloxypropoxy)phenyl]-s-triazine Following the general procedure of Example 7, 1.55 g (1.76 mmol) of 2,4-bis-[2-hydroxy-4-(2-hydroxy-3nonloxypropoxy)phenyl]-6-[4-(phenylthio)phenyl]-s-triazine are dissolved in 30 mL of chloroform. To the stirred solution at room temperature are added 0.606 g (1.76 mmol) of m-chloroperoxybenzoic acid (50–60%) all at once. After several minutes, the chloroform is removed under reduced pressure and the residue is redissolved in ethyl acetate. The solution is then washed five times with saturated sodium bicarbonate solution, once with water and once with brine and finally dried over anhydrous magnesium sulfate. The solvent is removed to give a yellow oil which is subjected to medium pressure liquid chromatography with 1:3 heptane:ethyl acetate. The title compound is isolated as a yellow glassy solid in a yield of 0.43 g (27%).

$^1$H nmr (CDCl$_3$) and mass spectra are consistent with the desired compound; UV $\lambda_{max}$ (CHCl$_3$) 304, 358 nm ($\epsilon$39,400, 37,300).

EXAMPLE 9

6-(p-Chlorophenyl)-2,4-bis-[2-hydroxy-4-(2-hydroxy-3-phenoxypropoxy)phenyl]-s-triazine Following the general procedure of Example 1, 1.94 g (4.80 mmol) of 6-(p-chlorophenyl)-2,4-(2,4-dihydroxyphenyl)-s-triazine, 7.76 g (51.7 mmol) of phenyl glycidyl ether and 120 mg of triphenylethylphosphonium iodide are heated for one hour at 180° C. The crude product is worked up by the procedure of Example 1 to yield a brown solid which is subjected to medium pressure liquid chromatography with 1:1 heptane:ethyl acetate to afford 2.21 g (65%) yield of the title compound as yellow crystals.

$^1$H nmr (CDCl$_3$) and mass spectra are consistent with the desired compound; UV $\lambda_{max}$ (ethyl acetate) 290, 334 nm ($\epsilon$30,200, 28,000).

In the following tests, the number of days to failure by delamination is reported. However, the time of year that the panel is exposed is very important due to the variability of sunlight intensity. Therefore, the number of days to failure may change if the panels are exposed in summer in contrast to exposure in winter.

EXAMPLE 10

2,4,6-Tris-(2,4-dihydroxy-5-hexylphenyl)-s-triazine

To a 500 mL, 3-necked round bottomed flask equipped with magnetic stirrer, a condenser, thermometer, HCl trap and a nitrogen atmosphere are charged 4.72 g (0.026 mol) of cyanuric chloride, 14.72 g (0.077 mol) of 4-hexylresorcinol, and 70 mL of tetrachloroethane. The 4-hexylresorcinol dissolves with gentle warming. Aluminum chloride (10.4 g, 0.078 mol) is added in small portions via Gooch tubing over about 40 minutes at room temperature. The solution turns from clear yellow to red during this period. The solution is stirred at 110° C. for two hours and is then allowed to cool to room temperature. A 300 mL portion of 2N hydrochloric acid is added and the mixture is refluxed for one hours during which time a color change from red to yellow occurs. The mixture is allowed to sit overnight and then is vacuum distilled. The residue is washed thrice with water and thrice with toluene to afford a brown solid swollen with tetrachloroethane. The residual solvent is removed under reduced pressure to afford 17.0 g (99% yield) of the title compound as a yellow solid, melting at >250° C.

$^1$H nmr (N-methylpyrrolidinone-d$_9$) and mass spectra are consistent with the desired compound; UV $\lambda_{max}$ (dimethylformamide) 308, 369 nm ($\epsilon$19,400; 33,600)

EXAMPLE 11

Delamination Resistance of High Solids Thermoset Acrylic Clear Coats Containing UV Absorbers Applied Directly over Electro Coat Primer Test panels are prepared by spray applying a 1.8–2.0 mil (0.036–0.051 mm) thick film of a commercially available high solids thermoset acrylic melamine clear coat, containing 2% by weight, based on the acrylic melamine resin, of a test UV absorber stabilizer, directly over 4"12" (10.16 cm×30.48 cm) UNIPRIME® panels obtained from Advance Coatings Technology, Inc. The coated panels are then baked at 250° F. (121° C.) for 30 minutes. After storage for one week in an air-conditioned room, the panels are exposed in Florida at 5° South, black box according to SAE J-1976. The panels are evaluated every day for delamination and are retired when delamination is evident on at least 10 percent of the panels. The results are shown in the table below.

| Test Compound of | Days to Delamination |
|---|---|
| Unstabilized | 19 |
| UVA 1* | 77 |
| Example 1 | 131 |
| Example 2 | 142 |
| Example 3 | 149 |

*UVA 1 is 2,4-bis-(2,4-dimethylphenyl)-6-(2-hydroxy-4-octyloxyphenyl)-s-triazine These data show that the instant compounds are essentially twice as effective as the prior art s-triazine UV absorber in preventing delamination of the clear coat from the electro coat primer.

EXAMPLE 12

Delamination Resistance of High Solids Thermoset Acrylic Clear Coats Containing UV Absorbers Applied Directly over Electro Coat Primer Following the procedure of Example 10, test panels, prepared by spray applying either a 0.9–1.0 mil (0.018–0.0254 mm) or a 1.8–2.0 mil (0.036–0.051 mm) thick film of a commercially available high solids thermoset acrylic melamine clear coat containing 2% by weight of a test stabilizer over panels, are exposed in Florida at 5° South, black box according to SAE J-1976. The days to delamination are recorded in the table below.

| Test Compound of | Days to Delamination 1 mil film | Days to Delamination 2 mil film |
|---|---|---|
| Unstabilized | 6 | 6 |
| UVA 1* | 25 | 30 |
| Example 2 | 47 | 61 |
| Example 3 | 40 | 59 |
| Example 6 | 47 | 54 |
| Example 7 | 41 | 69 |

*UVA 1 is 2,4-bis-(2,4-dimethylphenyl)-6-(2-hydroxy-4-octyloxyphenyl)-s-triazine These data show that the instant compounds are essentially twice as effective as the prior art s-triazine UV absorber in preventing delamination of the clear coat from the electro coat primer.

EXAMPLE 13

Gloss Retention of High Solids Thermoset Acrylic Clear Coats Containing UV Absorbers Applied Directly over a Silver Metallic Base Coat and a Electro Coat Primer A commercially available high solids thermoset acrylic clear coat is stabilized with 2.0 by weight, based on resin solids, of a s-triazine UV absorber test compound. Test panels are prepared by spray applying a 1.8–2.0 mil (0.072–0.102 mm) thick film of this stabilized clear coat over a commercially available silver metallic base coat, wet-on-wet, directly onto 4"×12" (10.16 cm×30.48 cm) UNIPRIME® panels obtained from Advanced Coating Technology, Inc. containing an electro coat primer. The coated panels are then baked at 250° F. (121° C.) for thirty minutes. The coated panels are then exposed in a Ci-65 Weather-O-meter (Atlas Electric Devices) according to ASTM G 26-90. The gloss of the exposed panels is measured at 300 hour intervals. Higher gloss indicates greater protecting afforded to the coating by the s-triazine UV absorber.

| Test Compound* | 20° Gloss (Hours of Xenon Arc Exposure) | | | | | | | | | |
|---|---|---|---|---|---|---|---|---|---|---|
| | 0 | 1164 | 2064 | 3004 | 4147 | 5111 | 6127 | 7287 | 7905 | 8859 |
| None | 92 | 81 | 66 | 51 | 34** | | | | | |
| T-1 | 94 | 83 | 85 | 86 | 79 | 73 | 59 | 47** | | |
| T-2 | 93 | 88 | 87 | 86 | 82 | 75 | 63 | 63 | 30** | |
| Ex. 1 | 94 | 88 | 87 | 87 | 83 | 77 | 67 | 55 | 45 | 22** |
| Ex. 2 | 93 | 88 | 89 | 88 | 85 | 78 | 71 | 75 | 61 | 37** |
| Ex. 3 | 94 | 86 | 87 | 88 | 84 | 78 | 66 | 64 | 53 | 29** |

*T-1 is 2,4-di(2,4-dimethylphenyl)-6-{2-hydroxy-4-[3-(2-ethylhexyl)oxy-2-hydroxypropoxy]-phenyl}-s-triazine.
T-2 is 2,4-di(2,4-dimethylphenyl)-6-[2-hydroxy-4-[3-tridecyloxy-2-hydroxypropoxy)phenyl]-s-triazine.
**The samples failed here by cracking.

It is clear from these data that the test compounds containing at least two groups on the triazinyl ring derived from resorcinol which is substituted in the para position by an alkoxy group which is in mm further substituted by hydroxyl and a further alkoxy moiety protect the coatings far better than the closest compounds of the prior art having only one moiety on the triazinyl ring derived from resorcinol.

EXAMPLE 14

Gloss Retention of High Solids Thermoset Acrylic Clear Coats Containing UV Absorbers Applied Directly over a Silver Metallic Base Coat and a Electro Coat Primer Coated panels prepared as in Example 13 are also exposed in a QUV exposure device (Q Panel Co.) according to ASTM G 53. The 20° glass is again measure at 300 hour intervals with higher gloss values indicating greater protection of the coating.

| Test Compound* | 20° Gloss (Hours of Xenon Arc Exposure) | | | | | | |
|---|---|---|---|---|---|---|---|
| | 0 | 267 | 606 | 905 | 1212 | 1515 | 1814 |
| None | 92 | 85 | 82 | 52** | | | |
| T-1 | 94 | 93 | 93 | 89 | 64 | 24** | |
| T-2 | 93 | 93 | 91 | 91 | 54 | 21** | |
| Ex. 1 | 94 | 94 | 93 | 91 | 84 | 52 | 27** |
| Ex. 2 | 93 | 94 | 93 | 90 | 83 | 49 | 32** |
| Ex. 3 | 94 | 94 | 92 | 91 | 81 | 58 | 16** |

*T-1 is 2,4-di(2,4-dimethylphenyl)-6-{2-hydroxy-4-[3-(2-ethylhexyl)oxy-2-hydroxypropoxy]-phenyl}-s-triazine.

T-2 is 2,4-di(2,4-dimethylphenyl)-6-[2-hydroxy-4-[3-tridecyloxy-2-hydroxypropoxy)phenyl] -s-triazine.

It is clear from these data that the test compounds containing at least two groups on the triazinyl ring derived from resorcinol which is substituted in the para position by an alkoxy group which is in turn further substituted by hydroxyl and a further alkoxy moiety protect the coatings far better than the closest compounds of the prior art having only one moiety on the triazinyl ring derived from resorcinol.

What is claimed is:
1. A tris-aryl-s-triazine compound of formula B or C

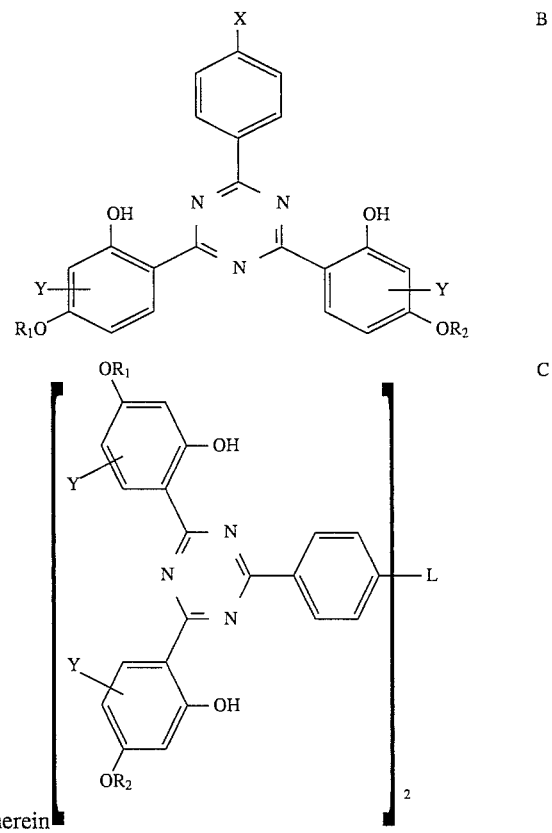

wherein
$R_1$ and $R_2$ are the same and are —$CH_2CH(OH)CH_2OR_5$,
$R_5$ is straight or branched chain alkyl of 1 to 24 carbon atoms, phenyl or said phenyl substituted by one to three halogen, alkyl of 1 to 8 carbon atoms, alkoxy of 1 to 8 carbon atoms or combinations thereof; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof;

Y is hydrogen or straight or branched chain alkyl of 1 to 6 carbon atoms;

X is —$SR_6$, —$SOR_6$ or —$SO_2R_6$, where $R_6$ is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms; and L is —S—, —SO—, —$SO_2$—, —S—S—, —S—E—S—, —SO—E—SO— or —$SO_2$—E—$SO_2$—, where E is alkylene of 2 to 12 carbon atoms, cycloalkylene of 5 to 12 carbon atoms or alkylene interrupted by or terminated by cyclohexylene; and with the proviso that, when X is —$SR_6$, —$SOR_6$ or —$SO_2R_6$, $R_1$ and $R_2$ can also be the same or different and are hydrogen or straight or branched chain alkyl of 1 to 24 carbon atoms; or said alkyl substituted by one to eight halogen, —$R_4$, —$OR_5$, —$N(R_5)_2$, —$CON(R_5)_2$, —$COOR_5$, or —$OCOR_5$ groups or combinations thereof; or said alkyl interrupted by one to eight —O—, —$NR_5$—, —$CONR_5$—, —COO—, —OCO—, or —CO— groups or combinations thereof; or said alkyl both substituted and interrupted by combinations of the groups mentioned above;

$R_4$ is cycloalkyl of 5 to 12 carbon atoms, straight or branched chain alkenyl of 2 to 18 carbon atoms, phenyl, naphthyl, biphenyl, or said phenyl, said naphthyl or said biphenyl substituted by one to three halogen, alkyl of 1 to 8 carbon atoms, alkoxy of 1 to 8 carbon atoms or combinations thereof; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof; and $R_5$ is defined as is $R_4$, or $R_5$ is also hydrogen or straight or branched chain alkyl of 1 to 24 carbon atoms.

2. The compound according to claim 1 which is 2,4-bis-(2,4-dihydroxyphenyl)-6-[4-(phenylthio)phenyl]-s-triazine;

2,4-bis-(4-butoxy-2-hydroxyphenyl)-6-[4-(phenylthio)phenyl]-s-triazine;

2,4-bis-[2-hydroxy-4-(2-hydroxy-3-nonyloxypropoxy)phenyl]-6-[4-(phenylthio)phenyl]-s-triazine;

6-[4-(benzenesulfonyl)phenyl]-2,4-bis-[2-hydroxy-4-(2-hydroxy-3-nonyloxypropoxy)phenyl]-s-triazine; or 6-[4-(benzenesulfinyl)phenyl]-2,4-bis-[2-hydroxy-4-(2-hydroxy-3-nonyloxypropoxy)phenyl]-s-triazine.

* * * * *